United States Patent [19]

Hegde

[11] Patent Number: 5,112,980
[45] Date of Patent: May 12, 1992

[54] PROCESS OF PREPARING SUBSTITUTED PYRIDINE COMPOUNDS

[75] Inventor: Shridhar G. Hegde, Maryland Heights, Mo.

[73] Assignee: Monsanto Company, St. Louis, Mo.

[21] Appl. No.: 702,573

[22] Filed: May 20, 1991

Related U.S. Application Data

[63] Continuation-in-part of Ser. No. 661,156, Feb. 27, 1991, abandoned, which is a continuation of Ser. No. 457,680, Dec. 27, 1989, abandoned.

[51] Int. Cl.$^5$ .............................. C07D 405/12
[52] U.S. Cl. .................... 546/283; 546/256; 546/268
[58] Field of Search ............... 546/256, 268, 283

[56] References Cited

U.S. PATENT DOCUMENTS 4,797,407  1/1989  Baker et al. .................... 546/283
4,931,450  6/1990  Sonnewald ..................... 546/283

Primary Examiner—C. Warren Ivy
Assistant Examiner—James H. Turnipseed
Attorney, Agent, or Firm—James C. Bolding; Stanley M. Tarter; Grace L. Bonner

[57] ABSTRACT

Disclosed herein is a process for cyclizing pyridinecarboxylate derivatives with 5-(haloalkyl) carboxamide or 5(haloalkyl)carbamate substitutions to prepare compounds useful as herbicides.

12 Claims, No Drawings

PROCESS OF PREPARING SUBSTITUTED PYRIDINE COMPOUNDS

REFERENCE TO A RELATED APPLICATION

The present application is a continuation-in-part application of application Ser. No. 07/661,156 filed Feb. 27, 1991, now abandoned, which is a continuation application of application Ser. No. 07/457,680, filed Dec. 27, 1989 (now abandoned).

BACKGROUND OF THE INVENTION

This invention relates to a process for preparation of a new class of 2,6-substituted pyridinedicarboxylic acid derivatives having activity as herbicides.

Pyridine derivatives have, for many years, been investigated for use in the biological sciences.

Pyridine dicarboxylate compounds useful as herbicides are described in U.S. Pat. No. 4,692,184. These compounds have fluorinated methyl groups at the 2- and 6-positions and carboxylic acids or their derivatives at the 3- and 5-positions and are characterized further by a 4-position substituent in which the atom attached to the pyridine ring is a carbon atom, such as alkyl, alkoxyalkyl, alkylthioalkyl, aralkyl, and like moieties.

More relevant compounds include those which contain fluorinated methyl groups at the 2- and 6-positions, carboxylic acids or their derivatives at the 3- and/or 5-positions and at the 4-position have a substituent group beginning with a hetero atom selected from O, S, N and P. These compounds are likewise useful as herbicides.

Other herbicidal pyridines are those of U.S. Pat. No. 4,609,399 which have a fluorinated methyl group at the 2-position, a carboxylic acid group or derivative thereof at the 3- and/or 5-position, and alkoxy groups at the 4- and 6-positions.

More relevant to the compounds prepared herein are those disclosed in U.S. Pat. No. 4,885,026 which are 5-amino pyridine 3-carboxylate derivatives.

BRIEF DESCRIPTION OF THE INVENTION

It is an object of this invention to provide a novel process for making certain pyridine compounds.

To achieve this object, a process is disclosed wherein a 5-(3-halopropylcarbonylamino)-, a 5-(4-halobutylcarbonylamino)-, or a 5-(2-haloethoxycarbonylamino)-derivative of a pyridine 3-carboxylate compound is cyclized under cyclizing conditions in the liquid phase in the presence of a Lewis acid catalyst to form a pyridine 5-cyclic imidate compound.

The compounds which are the starting materials for the process of this invention are represented by the generic formula

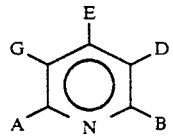

wherein:
one of A and B is selected from the group consisting of fluorinated methyl and chlorofluorinated methyl radicals, and the other is selected from the group consisting of fluorinated methyl, chlorofluorinated methyl and lower alkyl radicals;

E is selected from the group consisting of alkyl, alkenyl, cycloalkyl, cycloalkylalkyl, haloalkyl, and alkylthioalkyl radicals;

G is selected from the group consisting of hydroxycarbonyl, alkoxycarbonyl, haloalkoxycarbonyl, alkylthiocarbonyl, alkenyloxycarbonyl, alkynloxycarbonyl, cyano, pyridylthiocarbonyl, aminocarbonyl, disubstituted aminocarbonyl, and monosubstituted aminocarbonyl or is the same as D; and D is —NHR in which R is selected from the group consisting of 3-halopropylcarbonyl, 4-halobutylcarbonyl, and 2-haloethoxycarbonyl groups, each member of which is optionally substituted with one or more groups selected from alkyl, fluoro, chloro, bromo, iodo, alkylidene, alkoxy, alkylthio, and haloalkyl radicals.

Examples of alkoxycarbonyl include methoxycarbonyl, ethoxycarbonyl, propoxycarbonyl, etc. Examples of alkylthiocarbonyl include methylthiocarbonyl, ethylthiocarbonyl, propylthiocarbonyl, etc. Examples of alkenyloxycarbonyl include 2-propenylcarbonyl, 3-butenylcarbonyl, etc. Examples of pyridylthiocarbonyl include 2-pyridylthiocarbonyl, 3-pyridylthiocarbonyl, etc. Examples of chlorophenylamino include 4-chlorophenylamino, 3-chlorophenylamino, etc.

The compounds prepared by the process of this invention are those of the formula

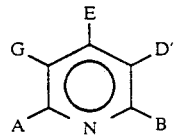

wherein:
one of A, B, G and E are defined as above, and
D' is selected from the group consisting of (tetrahydro-2(H)-pyran-2-ylidene)amino, (dihydro-2(3H)-furanylidene)amino, and (1,3-dioxolan-2-ylidene)amino groups, each member of which is optionally substituted on the ring portion with one or more groups selected from alkyl, fluoro, chloro, bromo, iodo, alkylidene, akloxy, alkylthio, and haloalkyl.

The Lewis acid catalyst employed in the cyclization process of this invention may be any such catalyst capable of achieving the cyclization reaction; however, presently preferred catalysts include silver tetrafluoroborate, ferric chloride, and zinc chloride.

As used herein throughout the specification and claims, the following terms have the following meanings:

The term "alkyl" and cognates thereof mean herein both straight and branched chain saturated hydrocarbon radicals having 1 to 7 carbon atoms, unless a different carbon number range is expressly stated. Examples of such radicals include, but are not limited to, ethyl, methyl, n-propyl, 1-ethylpropyl, 1-methylpropyl, n-butyl, 1,1-dimethylethyl, 2,2- dimethylpropyl, pentyl, isobutyl, isopropyl, and the like.

The term "cycloalkyl" means saturated cyclic radicals having 3 to 7 carbon atoms, such as cyclopropyl, cyclobutyl, cyclopentyl, cyclohexyl, and cycloheptyl.

The terms "alkenyl" and "alkynyl" herein mean alkenyl and alkynyl groups having 2 to 7 carbon atoms. Examples of such alkenyl groups include ethenyl, 1-propenyl, 2-propenyl, 1-butenyl, 2-butenyl, 3-butenyl, 2-methyl- 1-propenyl, 2-methyl-2-propenyl, 1-methylethenyl, and the like. Examples of such lower alkynyl groups include ethynyl, 1-propynyl, 2-propynyl, and so forth.

The term "cycloalkylalkyl" is intended to mean alkyl radicals having 1 to 3 carbon atoms which is substituted with a cycloalkyl group having 3 to 7 carbon atoms.

The term "haloalkyl" is intended to mean an alkyl radical (as defined above) substituted with one or more halogen atoms selected from F, Cl, Br, and I, "haloalkenyl" and "haloalkynyl" refer to alkenyl and alkynyl radicals substituted with one or more halogens.

The term "cation" means any monovalent cation derived from a base which is capable of forming a salt. Typical cations include, but are not limited to, alkali metals such as sodium, potassium, and lithium; alkaline earth metals such as calcium and magnesium; and ammonium salts, organic amines, sulfonium and phosphonium salts, and other salt complexes.

The term "fluorinated methyl" means herein methyl radicals having one or more fluorine atoms attached thereto, and includes radicals wherein all hydrogen atoms replaced by fluorine.

The term "chlorofluorinated methyl" means herein a methyl radical having at least one hydrogen replaced by fluorine and at least one other hydrogen replaced by chlorine.

The term "halogen" and its combining form "halo" are used herein to refer to fluorine, chlorine, bromine, and iodine.

The terms "disubstituted aminocarbonyl" and "monosubstituted aminocarbonyl" used to define G herein includes the N-substituents of monoalkyl, dialkyl, monophenyl, monophenylmethylene, monocycloalkyl and monocycloalkylalkyl.

DETAILED DESCRIPTION OF THE INVENTION

As used throughout the specification, including the Examples, the following abbreviations have the following meanings:

| LDA | lithium diisopropylamide |
|---|---|
| THF | tetrahydrofuran |
| DME | dimethoxyethane |
| DBU | 1,8-diazabicyclo-[5.4.0]-undec-7-ene |
| DMF | N,N-dimethylformamide |
| ETFAA | ethyl trifluoroacetoacetate |
| MCPBA | m-chloroperbenzoic acid |
| HPLC | high pressure liquid chromatography |
| TLC | thin layer chromatography |
| n-BuLi | n-Butyl lithium |
| DMSO | dimethyl sulfoxide |
| Pd/C | hydrogenation catalyst which is palladium deposited on finely-divided carbon |
| TsCl | tosyl chloride. |

Pyridine cyclic imidate compounds are prepared by cyclization of a pyridine haloalkyl carboxamide compound of this invention, which is in turn prepared by reaction of a 3- or 5-amino pyridine with a substituted or unsubstitued haloalkyl acid chloride. The 3- or 5-amino amino pyridine is prepared from a 3- or 5-chlorocarbonyl pyridine.

Aminopyridines and their preparation from the chlorocarbonyl pyridines (or pyridine acid chlorides) are described in more detail in U.S. Pat. No. 4,885,026.

Preparation of the chlorocabonyl pyridines (pyridine acid chlorides) is illustrated below in Steps 1-9. Preparation of the amino pyridines is shown below in Examples A-1 to A-7. Preparation of the haloalkylamides of this invention is shown in Examples 1 to 20, while preparation of the haloethoxy carboxamides (or haloethyl carbamates) is shown in Examples 21-23. Preparation of the pyridine cyclic imidate compounds of this invention is shown following these examples in Examples P-1 to P-22 which illustrative but not limitative of the invention.

PREPARATION OF PYRIDINE 5-ACID CHLORIDE STARTING MATERIALS

The compounds of this invention are prepared using as a starting material a pyridine 3,5-dicarboxylic acid mono-ester mono-chloride or dichloride. Steps 1-9 which follow set out in detail the preparation of three specific acid halides which are used as starting materials for the compounds of this invention. Other acid halides may be readily prepared using the procedures of Steps 1-9 by varying the ketoester and aldehyde used in Step 1 to obtain the desired substituents in the pyridinedicarboxylate product. Other suitable pyridinecarboxylate acid halides as starting materials are shown in U.S. Pat. No. 4,692,184 in Examples 44-51 and 82-83 inclusive, the disclosure of which is incorporated herein by reference in its entirety. Other acid halide starting materials may be readily prepared using the techniques set out in that U.S. Patent.

The following Steps 1-9 illustrate an example of the procedures for preparation of the acid halide compounds which are the starting materials for making the amides of the present invention. In these steps, a $\beta$-ketoester is reacted with an aldehyde to form a pyran (Step 1). The pyran is then reacted with ammonia to form a dihydroxypiperidine (Step 2), which is dehydrated to make a dihydropyridine compound (Step 3). The dihydropyridine is then oxidized or dehydrofluorinated to prepare a pyridinedicarboxylate compound (Step 4).

The ester groups of the pyridinedicarboxylate compound are the ester groups of the $\beta$-ketoester, and the 4-position of the pyridine is substituted with the same substituent as is on the aldehyde reagent.

When the pyridinedicarboxylate is substituted at the 2- or 6-position with a trifluoromethyl radical and at the other of these positions with a difluoromethyl radical, hydrolysis of the pyridine dicarboxylate compound occurs selectively on the side having the $CF_2H$ group when one equivalent of a base such as KOH is employed in the hydrolysis (Step 8). When two equivalents of base or more are employed, the dicarboxylate is hydrolyzed to the diacid (Step 5). The diacid may be converted to the diacid chloride by treatment with a chlorinating agent such as $SOCl_2$ or $PCl_5$. Following this conversion, treatment with one equivalent of an alcohol selectively esterifies the diacid chloride on the chloride group adjacent to the $CF_2H$ group.

STEP 1

Preparation of dimethyl 2,6-bis(trifluoromethyl)-2,6-dihydroxy-4-isobutyl-tetrahydro-3,5-pyran-dicarboxylate To a mechanically stirred mixture of 280 g (2.0 mole) of 80% pure methyl trifluoroacetoacetate and 86 g (1.0 mole) of isovaleraldehyde is added 1 ml of piperidine. An exothermic reaction occurs and the temperature of the reaction mixture reaches 105° C. After 5 hours of stirring, the reaction mixture is triturated with 450 ml of hexane and 30 ml of ether and cooled with a dry ice bath to give 1.68 g of a first crop, m.p. 83°–87° C. and 14.5 g of a second crop, m.p. 67°–73° C.

The first crop is the desired product which contains a mixture of 5:1 cis and trans isomers.

The second crop is a 2:1 mixture of cis and trans isomers. The mother liquor is concentrated to give 344 g of a residue which is a crude mixture of cis and trans isomer of the desired product.

STEP 2

Preparation of dimethyl 2,6-bis(trifluoromethyl)-2,6-dihydroxy-4-isobutyl-3,5-piperidinedicarboxylate To a solution of 344 g (0.920 mole) crude product from Step 1 in 500 ml of tetrahydrofuran (THF) is passed 58 g (3.41 mole) of gaseous ammonia for 3 hours. The reaction mixture is concentrated and the residue (332 g) is recrystallized from hexane-ether to give 53.7 g (13% yield from methyl trifluoroacetoacetate) of the desired product as a white solid, m.p. 102°–106° C.

The mother liquor is concentrated to provide more of the crude desired product.

STEP 3

Preparation of a 2:1 mixture of dimethyl 2,6-bis(trifluoromethyl)-1,4-dihydro-4-isobutyl-3,5-pyridinedicarboxylate isomer To an ice water cooled mixture of 200 ml of concentrated sulfuric acid and 200 ml of methylene chloride is added 48.7 g (0.115 mole) of the product of Step 2 at once. The reaction mixture is stirred for 20 minutes and poured into 1 L. of ice water. The methylene chloride layer is separated and washed once with 100 ml of saturated sodium bicarbonate, dried and concentrated to give 28.0 g (64.6%) of crude product. A portion (5.0 g) of this product is kugelrohr distilled at 0.5 torr (pot temperature at 120° C.) to give 4.8 g of the desired product, $n_D^{25}$ 1.4391.

Step 3 product may be prepared in better overall yield without isolation of Step 1 and Step 2 product by the following procedure:

To a mechanically stirred mixture of 340.3 g (1.98 mol) of 98.9% pure methyl trifluoroacetoacetate (MTFAA), 100 mL of toluene and 0.86 g (0.01 mol) of piperidine was added 90.5 g (1.03 mol) of isovaleraldehyde in 20 minutes. The reaction mixture exothermed causing a rise of temperature to 83° C. The reaction mixture was maintained at 80° C. for 3 hours. $^{19}$F NMR showed that the reaction was 89% complete. Heat was removed, and the reaction mixture was diluted with 125 mL of toluene and stirred overnight (16 hours). Gaseous ammonia was passed through the reaction mixture, the exotherm caused a rise of temperature to 68° C. in 50 minutes. A water cooling bath was applied to the reaction vessel to reduce the reaction temperature to 53° C. while ammonia was passed continuously. A total of 47.3 g (2.78 mol) of ammonia was passed in 1.5 hours. The reaction mixture was diluted with 100 mL of toluene. A Claisen distillation head was attached to the reaction vessel.

Excess ammonia and part of toluene were removed in vacuo (water aspirator) while the temperature was maintained at 26° C. An additional 200 mL of toluene was added, and the distillation was continued to remove a total of 200 mL of distillate in 1.5 hours. The reaction mixture was diluted with 100 mL of toluene and cooled to 5° C. with an ice bath. Sulfuric acid (453 g, 4.53 mol) was added in 5 minutes. The exotherm caused the temperature to rise to 25° C. The temperature gradually subsided to 5° C. in 10 minutes and was maintained at 5° C. for 40 minutes. An additional 95 g (0.95 mol) of sulfuric acid was added, and the reaction mixture was stirred at 5° C. for 20 minutes before being poured into a mixture of 500 mL of toluene and 2 L of ice water. The toluene layer was separated and the aqueous layer was extracted once with 500 mL of toluene. The combined toluene extracts were washed successively with 500 mL of water, 500 mL of saturated aqueous NaHCO$_3$, 500 mL of brine and concentrated in vacuo to 363.6 g of an oil. GC area percent analysis indicated that the oil contained 9% of 3,4-dihydropyridine isomer and 75.4% of 1,4-dihydropyridine isomer corresponding to an overall yield of 82.9% from MTFAA.

STEP 4

Preparation of dimethyl 2-(difluoromethyl)-6-(trifluoromethyl)-4-isobutyl-3,5-pyridinedicarboxylate.

(a) Reaction of the Product of Step 3 with DBU

A mixture of 23.0 g (0.0591 mole) of the product of Step 3, 12.2 g (0.077 mole) of 96% pure DBU, and 100 ml of THF is held at reflux for 3 days and poured into 250 ml of 3N HCl. The oil precipitate is extracted into ether (2×100 ml). The ether extracts are dried (MgSO$_4$) and concentrated to give 14.4 g of an oil which, according to $^1$H NMR, contained the desired product and acidic products. This oil is dissolved in ether and extracted with 10 ml of saturated sodium bicarbonate. The ether layer is dried (MgSO$_4$) and concentrated to give 8.9 g of an oil which is 71% pure desired product (by $^{19}$F NMR).

The sodium bicarbonate extract is acidified with concentrated HCl to give an oil which is extracted into ether. The ether layer is dried (MgSO$_4$) and concentrated to give 4.8 g of a residue which contained monocarboxylic acid and dicarboxylic acid (9:1) derived from the desired product. This residue is treated with 3.0 g (0.0217 mole) of potassium carbonate, 20 ml of methyl iodide, and 50 ml of acetone. The mixture is held at reflux for 42 hours and concentrated. The residue is treated with water and extracted with ether (2×100 ml). The ether layer is dried and concentrated. The residue is kugelrohr distilled at 1 torr (pot temperature of 130° C.) to give 5.1 g (23.4% from Step 3) of the desired product as an oil, $n_D^{25}$ 1.4478. This product crystallizes after standing, m.p. 36°–37° C.

The 71% pure desired product described previously was chromatographed by HPLC using 3% ethyl acetate/cyclohexane as eluent to give an earlier fraction (0.79 g, retention time 7–8.5 minutes) which was identified as methyl 6-(difluoromethyl)-4-(iso-butyl)-2-(trifluoromethyl)-3-pyridinecarboxylate. The second fraction (retention time 8.5–18.5 minutes) is an additional 6.4 g (29.4%) of pure desired product, $n_D^{25}$ 1.4474.

(b) Reaction of the Product of Step 3 with Tributylamine

A mixture of 38.9 g of an 80% pure product of Step 3 and 20.5 g of tributylamine is heated to 155° C. in 30 minutes. The reaction mixture was cooled to 30° C. and diluted with 100 ml of toluene. The toluene solution is washed successively with 6N hydrochloric acid, saturated sodium bicarbonate, and brine, dried and concentrated to give 36.4 g of a 73% pure product which corresponds to an 86% yield. This reaction can also be carried out in excess of tributylamine (10 equivalents) giving essentially similar results.

(c) Reaction of the Product of Step 3 with Tributylamine in Toluene

A mixture o 38.9 g of an 80% pure product of Step 3, 20.4 g of tributylamine and 30 ml of toluene is heated to 115° C. in 40 minutes and held at 115° C. for 1 hour and 40 minutes. The reaction mixture is cooled and worked up as in (b) above to give 36.3 g of a 76% pure product which corresponds to a 90% yield.

(d) Reaction of the Product of Step 3 with Tributylamine

A mixture of 11.8 g of an 80% pure product of Step 3 and 3.34 g of triethylamine is heated at 100° C. for 10 minutes, then at 125° C. for 10 minutes. The reaction mixture was cooled and worked up as in (b) above to give 8.14 g of a 76% pure product which corresponds to a 63% yield.

(e) Reaction of the Product of Step 3 With 2,6 Lutidine in the Presence of a Catalytic Amount of DBU A mixture of 5.0 g of product of Step 3 and 2.13 g of 2,6-lutidine is heated at 143° C. for 30 minutes. Two drops of DBU are added and the reaction mixture is heated for additional 1 hour and 30 minutes, cooled and worked up as in (b) above to give 4.23 g of the desired product. The reaction can also be carried out in excess of 2,6-lutidine and catalytic amount of DBU without solvent or in the presence of toluene as solvent giving similar results.

STEP 5

Preparation of 2-(difluoromethyl)-6-(trifluoro-methyl-4-isobutyl-3,5-pyridinedicarboxylic acid A 5-liter flask was charged with 894 g (2.42 mol) of the compound of Step 4 and 1 liter of water. To this was added a solution of 574 g (8.7 mol) of KOH in 800 ml of water. The mixture was refluxed overnight, after which HPLC showed that the reaction was complete. The flask was cooled to room temperature, acidified with HCl, and stirred until the organic phase solidified. The solids were filtered, washed with water, and dried in a fluid bed dryer. The diacid was obtained (756 g, 91.6% yield) as a brown solid.

STEP 6

Preparation of 3,5-bis-(chlorocarbonyl)-2-(difluoromethyl)-4-isobutyl-6-(trifluoromethyl)-pyridine The diacid product of Step 5 (37.06 g, 0.108 mole) was refluxed with 150 ml $SOCl_2$ for three hours. At this time, $^{19}F$ NMR indicated the reaction was complete. The excess $SOCl_2$ was removed by rotary evaporation, leaving a dark oil which was the bis-acid chloride. This was Kugelrohr distilled at 100° C. to give a colorless oil.

STEP 7

Preparation of methyl 5-chlorocarbonyl-2-(difluoromethyl)-4-isobutyl-6-(trifluoromethyl)-pyridine-3-carboxylate.

The product of Step 6 was then dissolved in 100 ml THF followed by 100 ml methanol. After 2½ hours the solvent was evaporated, leaving 31.2 g white solid, m.p. 71°-75° C. in 77% yield.

STEP 8

Preparation of 2-(difluoromethyl)-4-isobutyl-6-(trifluoromethyl)-3,5-pyridinedicarboxylic acid, 5-methyl ester A liter 4-necked flask was charged with 300 g of product of Step 4 and about 200 ml ethanol. In a separate flask was combined 59.14 g (0.896 mol) of 85% KOH and about 100 ml of water. The aqueous solution was poured into the organics and the flask was equipped with a mechanical stirrer, thermometer, nitrogen inlet and a water cooled condenser. The reaction mixture was heated to reflux, refluxed for 45 minutes and was cooled. The reaction mixture was concentrated and the concentrate was diluted with water and extracted once with ethyl ether. The ether extract (to remove starting material) was discarded. The aqueous solution was acidified with concentrated HCl and the orange precipitate that resulted was extracted with ethyl ether. The aqueous solution was extracted with ether 3 times. The ether extracts were combined and dried over anhydrous magnesium sulfate, filtered and concentrated to yield 253.13 g (87.5% yield) of the monoacid.

STEP 9

Preparation of methyl 2-(difluoromethyl)-3-chlorocarbonyl-4-isobutyl-6-(trifluoromethyl)-5-pyridinecarboxylate.

The acid (253 g, 0.7121 mol) from Step 8 was refluxed for 24 hours in approximately 250-300 ml of thionyl chloride. The reaction mixture was concentrated to yield 244.59 g of acid chloride in 91.9% yield. $n_D^{25}$ 1.4614.

Steps 1–9 above have illustrated the preparation of pyridine carboxylic acid chlorides having a particular set of 2,- 6,- and 4-substituents. Preparation of other acid chlorides will be clear from the foregoing and by reference to U.S. Pat. No. 4,692,184.

PREPARATION OF 5-AMINO PYRIDINES

The next step in the sequence for preparing compounds of the present invention is the conversion of the carboxylic acid chloride function of the starting materials shown above to the correspondingly-substituted 5-amino or 3,5-bis amino pyridine. The general procedure for this conversion is shown in Examples A-1 to A-7.

EXAMPLE A-1

3-Pyridinecarboxylic acid, 5-amino-2-(difluoromethyl)-4-(2-methylpropyl)-6-(trifluoromethyl)-, methyl ester To a stirred solution of 24.4 g (0.375 mol) sodium azide in 100 mL water and 200 mL of acetone at room temperature was added a solution of 55.8 g (0.15 mol) product of Step 7 above in 100 mL of acetone in portions. Following a mild exotherm, the mixture was stirred at room temperature for 4 h. The reaction mixture was concentrated, and diluted with 200 mL water. The mixture was extracted with ethyl ether (2×200 mL), and the combined extracts were washed with water (2×200 mL), dried (MgSO₄), and evaporated. The crude product was then vacuum distilled (130 C, 2mm Hg) by Kugelrohr apparatus to afford 44.0 g (91%) of the desired product as a pale yellow solid; mp 48°-50° C.

The following amines were made in a similar manner using the general procedure for Example A-1 and starting with the indicated pyridine acid chloride.

EXAMPLE A-2

3-Pyridinecarboxylic acid, 5-amino-4-cyclobutyl-2-(difluoromethyl)-6-(trifluoromethyl)-, methyl ester 90% yield from 3-pyridinecarboxylic acid, 5-chlorocarbonyl-4-cyclobutyl-2-(difluoromethyl)-6-(trifluoromethyl)-, methyl ester; mp 89°–93° C.

EXAMPLE A-3

3-Pyridinecarboxylic acid, 5-amino-2-(difluoromethyl)-4-methyl-6-(trifluoromethyl)-, methyl ester 61% yield 3-pyridinecarboxylic acid, 5-chlorocarbonyl-2-(difluoromethyl)-4-methyl-6-(trifluoromethyl)-, methyl ester; $n_D^{25} = 1.5844$.

EXAMPLE A-4

3-Pyridinecarbonitrile, 5-amino-6-(difluoromethyl)-4-(2-methylpropyl)-2-(trifluoromethyl)

89% yield from 3-pyridinecarbonitrile, 5-chlorocarbonyl-6-(difluoromethyl)-4-(2-methylpropyl)-2-(trifluoro-methyl)-.

EXAMPLE A-5

3-Pyridinecarboxylic acid, 5-amino-2-(difluoromethyl)-4-(cyclopropylmethyl)-6-(trifluoromethyl)-, methyl ester, 65% from 3-pyridinecarboxylic acid, 5-chlorocarbonyl-4-(cyclopropylmethyl)-2-(difluoromethyl)-6-(trifluoromethyl)-, methyl ester; $n_D^{25} = 1.5885$.

EXAMPLE A-6

3-Pyridinecarbothioic acid, 5-amino-2-(difluoromethyl)-4-(2-methylpropyl)-6-(trifluoromethyl)-, S-methyl ester 83% yield from 3-pyridinecarbothioic acid, 5-chlorocarbonyl-2-(difluoromethyl)-4-(2-methylpropyl)-6-(trifluoromethyl)-, S-methyl ester; $n_D^{25} = 1.5846$.

EXAMPLE A-7

3,5-Pyridinediamine, 2-(difluoromethyl)-4-(2-methylpropyl)-6-(trifluoromethyl

97% yield from 3,5-bis-(chlorocarbonyl)-2-(difluoromethyl)-4-(2-methylpropyl)-6-(trifluoromethyl) pyridine product of Step 6 above as a dark oil; used in further steps without purification, since this material is unstable.

PREPARATION OF COMPOUNDS OF THE INVENTION

The haloalkyl carbonxamide and haloethoxy carboxamide (or haloethyl carbamate) compounds of this invention are made as shown in the following Examples 1 to 23. Examples 1–20 illustrate the preparation of the haloalkyl carboxamide compounds, while Examples 21–23 illustrate synthesis of the haloethoxy carboxamide, or haloethyl carbamate, compounds.

EXAMPLE 1

3-Pyridinecarboxylic acid. 5-[(4-bromo-1-oxobutyl)amino]-4-cyclobutyl-2-(difluoromethyl)-6-(trifluoromethyl)-, methyl ester A stirred mixture of 5.10 g (0.016 mol) of product of Example A-2 and 3.63 g (0.020 mol) 4-bromobutyryl chloride in 40 mL anhydrous toluene was refluxed overnight. The mixture was allowed to cool to room temperature. Upon cooling, the precipitated product was collected by vacuum filtration on a Buchner funnel. Recrystallization in ethyl acetate-hexane provided 4.92 g (66%) of the desired product as an off-white solid: mp 167°–169 °C.

The amide compound in example 2 and the haloamide compounds of Examples 3 to 20 below were prepared using the same general procedure as that shown in Example 1.

EXAMPLE 2

3-Pyridinecarboxylic acid, 2-(difluoromethyl)-4-(2-methylpropyl)-5-[(1-oxo-4-pentenyl)amino]-6-(trifluoromethyl)-, methyl ester 63% yield from product of Example A-1 and 4-pentenoic acid chloride in THF solution at 75° C.; reaction time 3 d; mp 122°–124° C.

EXAMPLE 3

3-Pyridinecarbothioic acid, 5-[(4-bromo-1-oxobutyl)amino]-2-(difluoromethyl)-4-(2-methylpropyl)-6-(trifluoromethyl)-, S-methyl ester 65% yield from product of Example A-6 and 4-bromobutyryl chloride; reaction time 12 h; mp 147°–148° C.

EXAMPLE 4

3-Pyridinecarboxylic acid, 5-[(5-bromo-1-oxopentyl)amino]-2-(difluoromethyl)-4-(2-methylpropyl)-6-(trifluoromethyl)-, methyl ester 26% from product of Example A-1 and 5-bromopentanoyl chloride; reaction time 48 h; mp 94°–96° C.

EXAMPLE 5

3-Pyridinecarboxylic acid, 5-[(4-chloro-2-methyl-1-oxobutyl)amino]-2-(difluoromethyl)-4-(2-methylpropyl)-6-(trifluoromethyl)-, methyl ester 55% from product of Example A-1 and 4-chloro-2-methyl butyryl chloride; reaction time 48 h; mp 118°–120° C.

EXAMPLE 6

3-Pyridinecarboxylic acid, 5-[(4-chloro-3-methyl-1-oxobutyl)amino]-2-(difluoromethyl)-4-(2-methylpropyl)-6-(trifluoromethyl), methyl ester:

29% yield from product of Example A-1 and 4-chloro-3-methylbutanoyl chloride; reaction time 48 h; mp 109°–111° C.

EXAMPLE 7

3-Pyridinecarboxylic acid, 5-[(2,4-dichloro-1-oxobutyl)amino]-2-(difluoromethyl)-4-(2-methylpropyl)-6-(trifluoromethyl)-, methyl ester 68% from product of Example A-1 and 2,4-dichlorobutanoyl chloride; reaction time 12 h; mp 104°–106° C.

EXAMPLE 8

3-Pyridinecarboxylic acid, 5-[(4-bromo-2-methylene-1-oxobutyl)amino]2-(difluoromethyl)-4-(2-methylpropyl)-6-(trifluoromethyl)-, methyl ester 48% from product of Example A-1 and 4-bromo-2-(bromomethyl)butanoyl chloride; reaction time 4 d; mp 106°–108° C.

EXAMPLE 9

3-Pyridinecarboxylic acid, 5-[(4-bromo-2-methyl-1-oxobutyl)amino]-2-(difluoromethyl)-4-(2-methylpropyl)-6-(trifluoromethyl)-, methyl ester 81% from product of Example A-1 and 4-bromo-2-methylbutanoyl chloride; reaction was done neat at 60° C. overnight; mp 120°–122° C.

EXAMPLE 10

3-Pyridinecarboxylic acid, 5-[(4-bromo-2-fluoro-1-oxobutyl)amino]-2-(difluoromethyl)-4-(2-methylpropyl)-6-(trifluoromethyl, methyl ester 89% from product of Example A-1 and 4-bromo-2-fluorobutanoyl chloride at 60° C. overnight; mp 121°–122° C.

EXAMPLE 11

3-Pyridinecarboxylic acid, 5-[(4-bromo-1-oxobutyl)amino]-2-(difluoromethyl)-4-methyl-6-(trifluoromethyl)-, methyl ester 96% from product of Example A-3 and 4-bromobutanoyl chloride at 60° C. overnight; mp 98°–100° C.

EXAMPLE 12

Butanamide, N,N'-[2-(difluoromethyl)-4-(2-methylpropyl)-6-(trifluoromethyl)-3 5-pyridinediyl[bis[4-bromo]

32% from product of Example A-7 and 4-bromobutanoyl chloride at room temperature overnight; mp 234° C. (decomp.).

EXAMPLE 13

Butanamide, 4-bromo-N-5-cyano-2-(difluoromethyl)-4-(2-methylpropyl)-6-(trifluoromethyl)-3-pyridinyl]-

64% from product of Example A-4 and 4-bromobutanoyl chloride; mp 175°–180° C.

EXAMPLE 14

3-Pyridinecarboxylic acid, 5-[[4-bromo-2-(methylthio)-1-oxobutyl]amino]-2-(difluoromethyl)-4-(2-methylpropyl)-6-(trifluoromethyl)-, methyl ester 61% from product of Example A-1 and 4-bromo-2-(methylthio)butanoyl chloride at 60°–80° C. for 30 h; mp 103–105° C.

EXAMPLE 15

3-pyridinecarbothioic acid, 5-[(4-bromo-2-methyl-1-oxobutyl)amino]-2-(difluoromethyl)-4-(6-(trifluoromethyl)-, S-methyl ester 97% yield from product of Example A-6 and 4-bromo-2-methyl butanoyl chloride; m.p. 120°–121° C.

EXAMPLE 16

3-Pyridinecarboxylic acid, 5-(4-bromo-2,2-dimethyl-1-oxobutyl)amino]-2-(difluoromethyl)-4-(2-methylpropoyl)-6-(trifluoromethyl)-, methyl ester 33% from product of of Example A-1 and 4-bromo-2,2-dimethyl butanoyl chloride; reaction time 96 h.

EXAMPLE 17

3-Pyridinecarboxylic acid, 5-[(2-bromo-4-iodo-1-oxobutyl)amino]-2-(difluoromethyl)-4-(2methylpropyl)-6-(trifluoromethyl)-, methyl ester A stirred mixture of 5.62 g (0.010 mol) of product of Example 20 and 1.63 g (0.010 mol) of sodium iodide in 30 mL acetone was refluxed for 1 hour. The solvent was evaporated, and the residue was partitioned between water (100 mL) and ethyl ether (150 mL). The organic layer Was washed with water (2×30 mL), dried (MgSO$_4$) and evaporated. The crude material was filtered through silica gel, and trituration of the oily residue with hexane/ethyl ether afforded 4.72 g (78%) of the desired product as a white solid; mp 111°–113° C.

EXAMPLE 18

3-Pyridinecarboxylic acid, 5-[4-bromo-1-(oxobutyl)amino]-2(difluoromethyl)-4-(2-methylpropyl)-6-(trifluoromethyl)-, methyl ester 72% from product of Example A-1; m.p. 95°–96° C.

EXAMPLE 19

3-Pyridinecarboxylic acid, 5-[(4-bromo-1-oxobutyl)amino]-4-(cyclopropylmethyl)-2-(difluoromethyl)-6-(trifluoromethyl)-, methyl ester 70% yield from product of Example A-5; mp 60°–61° C.

EXAMPLE 20

3-Pyridinecarboxylic acid, 5-[(2,4-dibromo-1-oxobutyl)amino]-2-(difluoromethyl)-4-(2-methylpropyl)-6-(trifluoromethyl)-, methyl ester 31% from product of Example A-1 and 2,4-dibromobutyryl chloride; reaction time 72 h; mp 113°–115° C.

The following Examples 21–23 show the haloethyl carbamate compounds of this invention which are precursor compounds to the cyclic imidate compounds containing two oxygen atoms in the heterocycle attached to the pyridine ring. Each of these compounds is prepared by reaction of a chlorocarbonyl pyridine with sodium azide in the presence of an appropriate 1,2-diol to form a hydroxyethyl carbamate (Step A), followed by chlorination (Step B). Example 21 shows the procedure in detail, and the compounds of Examples 22 and 23 are prepared similarly.

EXAMPLE 21

3-Pyridinecarboxylic acid, 5-[[2-chloroethoxy)carbonyl]amino]-2-(difluoromethyl)-4-(2-methylpropyl)-6-(trifluoromethyl)-, methyl ester

Step A

3-Pyridinecarboxylic acid, 2-(difluoromethyl)-5-[(2-hydroxyethoxy) carbonyl]amino]-4-(2-methylpropyl)-6-(trifluoromethyl)-, methyl ester To a stirred suspension of 7.8 g (0.12 mol) of sodium azide in a mixture of 100 mL of ethylene glycol and 100 mL of acetone was added a solution of 18.6 g (0.05 mol) of the 5-chlorocarbonyl pyridine shown in Step 7 above in 50 mL of acetone in small portions. The reaction mixture was stirred at room temperature overnight, and then concentrated to remove most of the acetone. The mixture was diluted with water and extracted with three 200 mL portions of ethyl acetate. The combined organic layers were washed with water, dried over anhydrous magnesium sulfate, and evaporated. Purification of the residue by HPLC gave 16.6 g (80%) of intermediate as a white solid: mp 104° C.

Step B

A solution of 13.6 g (0.033 mol) of product of Step A in 100 mL of thionyl chloride was refluxed for 4 h. The solution was then evaporated and the residue was partitioned between 200 mL of chloroform and 200 mL of water. The organic layer was dried over anhydrous magnesium sulfate and evaporated. Purification of the residue by HPLC afforded 10.6 g (74%) of title compound as a white solid: mp 95°–96° C.

EXAMPLE 22

3-Pyridinecarboxylic acid, 5-[[(2-chloroethoxy)carbonyl]amino]-2-(difluoromethyl-4-(2-methylpropyl-6-trifluoromethyl)-, methyl ester

Step A

3-Pyridinecarboxylic acid, 2-(difluoromethyl)-5-[[(2-hydroxypropoxy)carbonyl]amino]-4-(2-methylpropyl-6-(trifluoromethyl)-, methyl ester 63% yield from product of Step 7 above and sodium azide in propylene glycol/acetone; mp 97°–99° C.

Step B 79.8% yield from Step A; mp 94°–96° C.

EXAMPLE 23

3-Pyridinecarboxylic acid, 5-[[(2-chloro-1-methylpropoxy)carbonyl[amino]-2-(difluoromethyl)-4-(2-methylpropyl)-6-(trifluoromethyl)-, methyl ester

Step A

3-Pyridinecarboxylic acid, 2-(difluoromethyl)-5-[[2-hydroxy-1-methylpropoxy)carbonyl]amino]-4-(2-methyl propyl)-6-(trifluoromethyl), methyl ester 52 5% yield from product of Step 7 above and sodium azide in 2,3-butanediol/acetone; mp 137°–138° C.

Step B

88% yield from Step A; mp 108°–110° C.

PREPARATION OF CYCLIC IMIDATE COMPOUNDS

Preparation of the pyridine cyclicimidate compounds from the haloalkyl carboxamide and haloethoxy carboxamide compounds using the process of this invention is shown in the following Examples P-1 to P-22.

EXAMPLE P-1

3-Pyridinecarboxylic acid, 2-(difluoromethyl)-4-(2-methylpropyl)-5-[tetrahydro-2H-pyran-2-ylidene)amino]-6-(trifluoromethyl)-, methyl ester To a stirred solution of 2.87 g (0.0059 mol) of product of Example 4 in 75 mL methylene chloride was added 1.30 g (0.0067 mol) silver tetrafluoroborate in one portion at room temperature. The resulting slurry was stirred for 30 min. and, this was followed by addition of 100 ml of sat. sodium bicarbonate solution for an additional 30 min. The mixture was vacuum filtered through a celite pad to remove the precipitated silver salts. The filtrate layers were separated, and the organic layer was dried (MgSO₄) and evaporated. The crude material was purified by HPLC (20% ethyl acetate-hexane) to afford 1.60 g (67%) of the desired product as a pale yellow wax: $n_D^{25} = 1.58475$;

EXAMPLE P-2

3-Pyridinecarboxylic acid, 2-(difluoromethyl)-5-[(dihydro-3-methyl-2(3H)-furanylidene)amino]-4(2-methylpropyl)-6-(trifluoromethyl)-, methyl ester To a stirred solution of 2.00 g (0.0045 mol) of product of Example 5 in 25 mL methylene chloride was added 1.05 g (0.0054 mol) silver tetrafluoroborate in one portion. The resulting slurry was stirred for 1 h, and this was followed by the addition of 100 mL sat. sodium bicarbonate and stirring for an additional 30 min. The mixture was filtered through celite to remove the precipitated silver salts, and the layers were separated. The organic layer was dried (MgSO₄) and evaporated. The residue was purified by chromatography (20% ethyl acetate-hexane) to afford 1.30 g (71%) of the desired product as a clear colorless wax; $n_D^{25} = 1.5820$;

This compound may be similarly prepared using the product of Example 9.

The following compounds of Examples P-3 to P-16 were made by the same general process as those shown above in Examples P-1 and P-2.

EXAMPLE P-3

3-Pyridinecarboxylic acid, 2-(difluoromethyl)-5-dihydro-4-methyl-2(3H)-furanylidene)amino]-4-(2-methyl-propyl)-6-(trifluoromethyl-, methyl ester 84% yield from product of Example 6; $n_D^{25} = 1.5822$.

EXAMPLE P-4

3-Pyridinecarboxylic acid,
5-[(3-bromodihydro-2(3H)-furanylidene)amino]-2-(difluoromethyl)-4-(2-methylpropyl)-6-(trifluoromethyl)-, methyl ester 64% from product of Example 17; $N_D^{25} = 1.5842$.

EXAMPLE P-5

3-Pyridinecarboxylic acid,
5-[3-chlorodihydro-2-(3H)-furanylidene)amino]-2-(difluoromethyl)-4-(2-methylpropyl)-6-(trifluoromethyl)-, methyl ester 77% from product of Example 7; $n_D^{25} = 1.5836$.

EXAMPLE P-6

3-Pyridinecarboxylic acid,
2-(difluoromethyl)-5-[(dihydro-3,3-dimethyl-2(3H)-furanylidene]amino]-4-(2-methylpropyl)-6-(trifluoromethyl)-, methyl ester 34% from product of Example 16; $n_D^{25} = 1.5850$.

EXAMPLE P-7

3-Pyridinecarboxylic acid,
2-(difluoromethyl)-5-[3-fluorodihydro-2(3H)-furanylidene)amino]-4-(2-methylpropyl)-6-(trifluoromethyl)-, methyl ester 80% from product of Example 10; $n_D^{25} = 1.5825$.

EXAMPLE P-8

3-Pyridinecarboxylic acid,
2-(difluoromethyl)-5-[(dihydro-3-methylene-2(3H)-furanylidene)amino]-4-(2-methylpropyl)-6-(trifluoromethyl)-,methyl ester 66% from product of Example 8; $n_D^{25} = 1.5802$.

EXAMPLE P-9

3-Pyridinecarboxylic acid,
2-(difluoromethyl)-5-[(dihydro-2(3H)-furanylidene)amino]-4-methyl-6-(trifluoromethyl)-methyl ester 79% from product of Example 11; $n_D^{25} = 1.5842$.

EXAMPLE P-10

3,5-Pyridinediamine,
2-(difluoromethyl)-N,N'-bis(dihydro-2(3H)-furanylidene)-4-(2-methylpropyl)-6-(trifluoromethyl)

84% from product of Example 12; mp 98°–102° C.

EXAMPLE P-11

3-Pyridinecarbonitrile
6-(difluoromethyl)-5-[(dihydro-2(3H)-furanylidene)amino]-4-(2-methylpropyl)-6-(trifluoromethyl)

55% from product of Example 13; mp 68°–69° C.

EXAMPLE P-12

3-Pyridinecarboxylic acid,
2-(difluoromethyl)-5-[[(dihydro-3-(methylthio)-2-(3H)-furanylidene)amino]-4-(2-methylpropyl)-6-(trifluoromethyl),methyl ester 81% from product of Example 14; $n_D^{25} = 1.5860$.

EXAMPLE P-13

3-Pyridinecarboxylic acid,
4-cyclobutyl-2-(difluoromethyl)-5-[(dihydro-2(3H)-furanylidene)amino]-6-(trifluoromethyl)-, methyl ester 56% from product of Example 1; $n_D^{25} = 1.586$.

EXAMPLE P-14

3-Pyridinecarbothioic acid,
2-(difluoromethyl)-5-[(dihydro-2(3H)-furanylidene)amino]-4-(2-methylpropyl)-6-trifluoromethyl)-, S-methyl ester 72% from product of Example 3; mp 89°–91° C.

EXAMPLE P-15

Pyridinecarboxylic acid,
2-(difluoromethyl)-5-[(dihydro-2(3H)-furanylidene)amino]-4-(2-methylpropyl)-6-(trifluoromethyl)-, methyl ester 71% from product of Example 18; $n_D^{25} = 1.5876$.

EXAMPLE P-16

3-Pyridinecarboxylic acid, 4-(cyclopropylmethyl)-2-(difluoromethyl)-5-[(dihydro-2(3H)-furanylidene)amino]-6-(trifluoromethyl)-, methyl ester 91% from product of Example 19; $n_D^{25} = 1.5865$.

EXAMPLE P-17

3-Pyridinecarboxylic acid,
5-[[5-(bromomethyl)dihydro-2(3H)-furanylidene]amino]-2-(difluoromethyl)-4-(2-methylpropyl)-6-(trifluoromethyl)-, methyl ester To a mixture of 3.38 g (0.0083 mol) of product of Example 2 in 100 mL carbon tetrachloride was added sufficient methylene chloride to dissolve the amide completely. To this solution was added a solution of 1.32 g (0.0083 mol) of bromine in 25 mL caron tetrachloride dropwise at room temperature. Following the addition, the reaction mixture was partitioned with 100 mL 25% sodium thiosulfate solution, and the layers were separated. The organic layer was dried (MgSO$_4$) and evaporated. The crude product (4,5 dibromobutyramide) was dissolved in 50 mL methylene chloride. To this solution was added 1.62 g (0.0083 mol) silver tetrafluoroborate with stirring in one portion. After 30 min., saturated sodium bicarbonate solution (50 mL) was added with stirring for an additional 10 min. The reaction mixture was vacuum filtered through celite and the layers were separated. The organic layer was dried (MgSO$_4$) and evaporated. The crude material was purified by HPLC (20% ethyl acetate-hexane) to afford 3.19 g (79%) of the desired product as a pale yellow viscous oil: $n_D^{25} = 1.5827$.

EXAMPLE P-18

3-Pyridinecarbothioic acid,
2-(difluoromethyl)-5-[(dihydro-2(3H)-thienylidene)amino]-4-(2-methyloropyl)-6-(trifluoromethyl)-, S-methyl ester A slurry of 5.51 g (0.011) product of Example 3 and 2.45 g (0.012 mol) of phosphorous pentachloride in 60 mL carbon tetrachloride was stirred overnight at room temperature. The resulting clear solution was concentrated in vacuo to afford 5.70 g (100%) of the desired intermediate as a clear oil with no further purification necessary. A slurry of this oil and 0.72 g (0.016 mol) of lithium sulfide in 30 mL anhydrous THF was stirred at room temperature overnight. The solvent was evaporated, and the residue was partitioned with ethyl ether (150 mL) and 10% HCl (150 mL). The organic layer was dried (MgSO₄) and evaporated. The crude material was purified by HPLC (15% ethyl acetate-hexane) to afford 1.54 g (35%) of the desired product as a clear wax; $n_D^{25} = 1.5842$.

EXAMPLE P-19

3-Pyridinecarbothioic acid, 2-(difluromethyl)-5-[(dihydro-3-methyl-2(3H)-furanylidene)amino]-4-(2-methylpropyl)-6-(trifluoromethyl)-S-methyl ester 42% from product of Example 15; $n_D^{25} = 1.5950$.

EXAMPLE P-20

3-Pyridinecarboxylic acid, 2-(difluoromethyl-5-(1,3-dioxolan-2-ylidene]amino-4-(2-methylpropyl-6-(trifluoromethyl)-, methyl ester To a solution of 6.48 g (0.015 mol) of product of Example 22 in 200 mL of methylene chloride was added 3.3 g (0.017 mol) of silver tetrafluoroborate in one portion. The resulting suspension was stirred at room temperature for 10 h after which 200 mL of saturated sodium bicarbonate solution was added and stirring was continued for an additional 45 min. The mixture was filtered to remove insoluble salts and the salts were washed with 200 mL of methylene chloride. The organic layer in the combined filtrates was separated, dried over anhydrous magnesium sulfate, and evaporated. Purification of the residue by HPLC afforded 5.5 g (92.6%) of title compound as a white solid: mp 101°-102° C.

Examples P-21 and P-22 were each prepared similarly to Example P-20.

EXAMPLE P-2

3-Pyridinecarboxylic acid, 2-(difluoromethyl)-5-[(4-methyl-1,3-dioxolan-2-ylidene)amino]-4-(2-methylpropyl)-6-(trifluoromethyl)-, methyl ester 73% yield from product of Example 22 as a colorless oil; $n_D^{25} = 1.5955$.

EXAMPLE P-23

3-Pyridinecarboxylic acid, 2-(difluoromethyl)-5-(4,5-dimethyl-1,3-dioxolan-2-ylidene)amino]-4-(2-methylpropyl)-6-(trifluoromethyl)-, methyl ester 75.5% yield from product of Example 22 as a colorless oil; $n_D^{25} = 1.5982$.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of the patentable novelty which reside in the present invention, including all features which would be treated as equivalents thereof by those skilled in the art to which the invention pertains.

We claim:
1. A process for cyclizing a compound of the formula

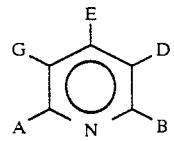

wherein:
one of A and B is selected from the group consisting of fluorinated methyl and chlorofluorinated methyl radicals, and the other is selected from the group consisting of fluorinated methyl, chlorofluorinated methyl and lower alkyl radicals;

E is selected from the group consisting of alkyl, alkenyl, cycloalkyl, cycloalkylalkyl, haloalkyl, and alkylthioalkyl radicals;

G is selected from the group consisting of hydroxycarbonyl, alkoxycarbonyl, haloalkoxycarbonyl, alkylthiocarbonyl, alkenyloxycarbonyl, alkynloxycarbonyl, cyano, pyridylthiocarbonyl, aminocarbonyl, disubstituted aminocarbonyl, and monosubstituted aminocarbonyl or is the same as D; and D is —NHR in which R is selected from the group consisting of 3-halopropylcarbonyl, 4-halobutylcarbonyl, and 2-haloethoxycarbonyl groups, each member of which is optionally substituted with one or more groups selected from alkyl, fluoro, chloro, bromo, iodo, alkylidene, alkoxy, alkylthio, and haloalkyl radicals, to form a compound of the formula

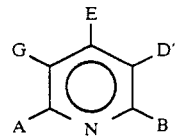

wherein:
one of A, B, G and E are defined as above, and
D' is selected from the group consisting of (tetrahydro-2(H)-pyran-2-ylidene)amino, (dihydro-2(3H)-furanylidene)amino, and (1,3-dioxolan-2-ylidene)amino groups, each member of which is optionally substituted on the ring portion with one or more groups selected from alkyl, fluoro, chloro, bromo, iodo, alkylidene, alkoxy, alkylthio, and haloalkyl, which comprises cyclizing the starting compound in the liquid phase under cyclizing conditions in the presence of a Lewis acid catalyst.

2. A process according to claim 1 wherein the Lewis acid catalyst is selected from silver tetrafluoroborate, ferric chloride, and zinc chloride.

3. A process according to claim 2 wherein one of A and B is trifluoromethyl and the other is difluoromethyl.

4. A process according to claim 3 wherein E is selected from the group consisting of 2-methylpropyl, cyclobutyl, and cyclopropylmethyl.

5. A process according to claim 4 wherein D' is (dihydro-2(3H)-furanylidene)amino.

6. A process according to claim 5 wherein D' is substituted at the 3-position of the ring with a methyl group.

7. A process according to claim 5 wherein D' is substituted at the 3-position of the ring with a member selected from the group consisting of fluoro and chloro.

8. A process according to claim 1 wherein G is alkoxycarbonyl.

9. A process according to claim 8 wherein G is methoxycarbonyl.

10. A process according to claim 5 wherein G is alkoxycarbonyl.

11. A process according to claim 10 wherein G is methoxycarbonyl.

12. A process according to claim 6 wherein G is methoxycarbonyl.

* * * * *